(12) United States Patent
Cattadoris et al.

(10) Patent No.: US 8,216,828 B2
(45) Date of Patent: Jul. 10, 2012

(54) ASSEMBLY OF CELL CULTURE VESSELS

(75) Inventors: Henry J. Cattadoris, Scarborough, ME (US); Gregory R. Martin, Acton, ME (US); Allison J. Tanner, Portsmouth, NH (US)

(73) Assignee: Corning Incorporated, Corning, NY (US)

( * ) Notice: Subject to any disclaimer, the term of this patent is extended or adjusted under 35 U.S.C. 154(b) by 524 days.

(21) Appl. No.: 12/211,430

(22) Filed: Sep. 16, 2008

(65) Prior Publication Data

US 2009/0298164 A1  Dec. 3, 2009

Related U.S. Application Data

(60) Provisional application No. 61/130,421, filed on May 30, 2008.

(51) Int. Cl.
*C12M 1/12* (2006.01)
*C12M 3/00* (2006.01)
*C12M 1/24* (2006.01)
*B29C 35/08* (2006.01)
*B29C 35/00* (2006.01)

(52) U.S. Cl. ............... 435/297.5; 435/294.1; 435/297.1; 435/304.2; 435/304.3; 264/492; 264/493; 264/494

(58) Field of Classification Search ............... 435/297.5, 435/294.1, 297.1, 304.2, 304.3; 264/492, 264/493, 494
See application file for complete search history.

(56) References Cited

U.S. PATENT DOCUMENTS

| | | |
|---|---|---|
| 2002/0022219 A1 | 2/2002 | Clements et al. |
| 2005/0047971 A1 | 3/2005 | Clements et al. ............. 422/102 |
| 2007/0026516 A1 | 2/2007 | Martin et al. |

FOREIGN PATENT DOCUMENTS

WO  WO 2007/015770  2/2007

OTHER PUBLICATIONS

Branson Ultrasonics Corporation, "Plastics Joining Technology Overview", http://www.branson-plasticsjoin.com/how_tech_works.asp.
Leister Technologies, LLC, "Laser Systems for Weling Thermoplastics and Selective Soldering", http://www.leisterlaser.com/.
Branson Ultrasonics Corporation, "Laser Welding System", http://branson-piasticsjoin.com/laser_systems.asp.

*Primary Examiner* — Nathan Bowers
*Assistant Examiner* — Gautam Prakash
(74) *Attorney, Agent, or Firm* — Susan S. Wilks

(57) ABSTRACT

A cell culture apparatus includes a cell culture chamber formed by a first major surface, an opposing second major surface spaced apart from the first major surface, and a first side wall around the first chamber and extending between the first and second major surfaces. A portion of the first sidewall proximate the first major surface comprises an infrared absorbent material, and a portion the first sidewall proximate the second major surface is formed from substantially non-infrared absorbent material. The first major surface is formed by a gas permeable polymeric film that is impermeable to cell culture liquid.

19 Claims, 14 Drawing Sheets

US 8,216,828 B2

ASSEMBLY OF CELL CULTURE VESSELS

CLAIMING BENEFIT OF PRIOR FILED U.S. APPLICATION

This application claims the benefit of U.S. Provisional Application Ser. No. 61/130,421, filed on May 30, 2008. The content of this document and the entire disclosure of publications, patents, and patent documents mentioned herein are incorporated by reference.

FIELD

The present disclosure relates to vessels for culturing cells and to methods for assembling such vessels.

BACKGROUND

Some currently available cell culture vessels such as T-flasks, Triple Flasks, and Cell Factories are multi-component assemblies that are bonded together via ultrasonic welding. Ultrasonic welding is desirable due to its low cost and lack for need of any additional material for bonding. However, ultrasonic welding generates particulate that can contaminate the culture chamber. Some multi-component assembled cell culture vessels avoid this particulate generation by utilizing a UV cure adhesive during assembly. Using a foreign material such as an adhesive, however, increases the number of materials of construction leading to increased potential for undesirable interactions between these materials and some cell types.

BRIEF SUMMARY

The present disclosure provides cell culture articles and manufacturing methods that avoid particulate generation by laser welding components of the cell culture article together. An infrared absorbing material is present at the interface to be welded, and an infrared emitting source, such as an infrared laser diode, is directed at the interface to weld the components together. Infrared absorbent materials such as carbon black can be blended into one of the polymers at the interface to act as a laser absorber. Carbon black does not pose a significant interaction risk with the cells in culture as it is largely unable to migrate from the polymer due to the high molecular weight and large physical dimensions of carbon black relative to intramolecular spacing of the polymer into which carbon black is incorporated.

In an embodiment, the disclosure provides a cell culture apparatus. The apparatus includes a cell culture chamber formed by a first major surface, an opposing second major surface spaced apart from the first major surface, and a first side wall around the first chamber and extending between the first and second major surfaces. A portion of the first sidewall proximate the first major surface comprises an infrared absorbent material, and a portion the first sidewall proximate the second major surface is formed from substantially non-infrared absorbent material. The first major surface is formed by a gas permeable polymeric film that is impermeable to cell culture liquid.

In an embodiment, the disclosure provides a method for manufacturing a cell culture article. The method includes molding a frame that has an optically transparent major surface and a sidewall extending from the major surface. The sidewall has an optically transparent portion proximate the major surface and an infrared absorbent portion distal the major surface. The molding includes (i) introducing a first polymeric composition into a mold for forming the transparent major surface and transparent portion of the sidewall, (ii) and introducing into the mold a second polymeric composition including an infrared absorbent material for forming the infrared absorbent portion of the sidewall distal the major surface. The method further includes contacting the infrared absorbent portion of the sidewall to a gas permeable polymeric film to form an interface between the sidewall and film. The method also includes directing infrared radiation to the interface to sufficiently melt the infrared absorbent portion of the sidewall to sealingly bond the frame to the film such that a chamber for culturing cells is formed by a surface of the film, the major surface of the frame and the sidewall.

The culture apparatuses described herein may be made such that the cell culture chamber contains reduced amounts of particulate matter or cell culture interfering materials associated with existing methods. This and other advantages will be readily understood from the following detailed descriptions when read in conjunction with the accompanying drawings.

BRIEF DESCRIPTION OF THE DRAWINGS

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

Figure 1A:
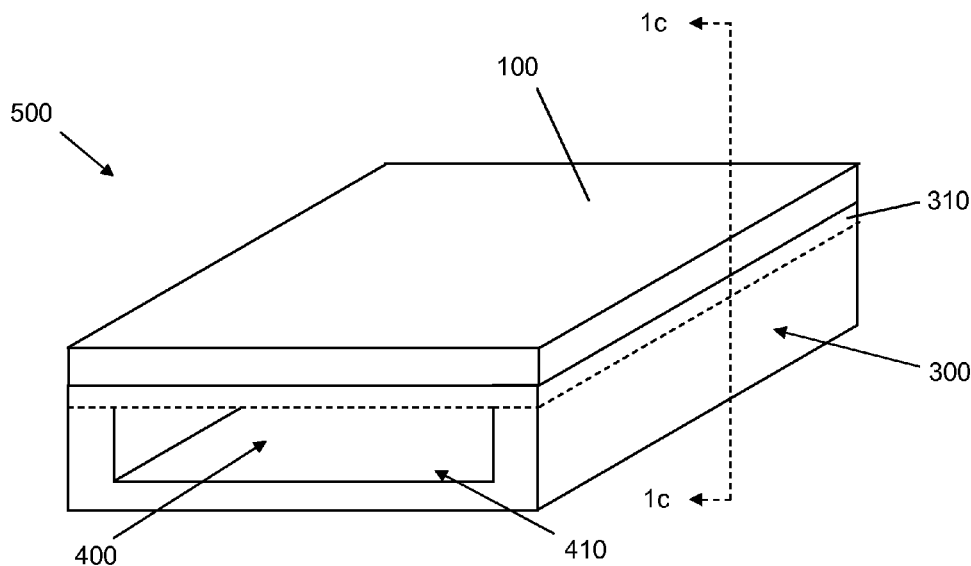
FIG. 1A is a schematic perspective view of a representative cell culture assembly.

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

As used herein, a "non-infrared absorbing material" and the like, mean a material that does not sufficiently absorb infrared radiation during a infrared laser welding process to heat sufficiently to melt material into which the "non-infrared absorbing material" is incorporated.

The present disclosure describes, inter alia, cell culture articles having cell culture chambers that may contain reduced amounts of particulate matter or cell culture interfering materials that are associated with existing methods for manufacturing the articles. The cell culture articles and manufacturing methods described herein avoid particulate generation and contamination issues by laser welding components of the cell culture article together. An infrared absorbing material is present at the interface to be welded, and an infrared emitting source, such as an infrared laser diode, is directed at the interface to weld the components together. Infrared absorbent materials such as carbon black can be blended into one of the polymers at the interface to act as a laser absorber. Such infrared absorbent materials do not pose a significant interaction risk with the cells in culture as they are largely unable to migrate from the polymer due to the high molecular weight and large physical dimensions of carbon black relative to intramolecular spacing of the polymer into which infrared absorbing material is incorporated.

Nearly any cell culture article assembled from multiple parts can be readily adapted to be formed as described herein. Cell culture vessels where a cell culture chamber is formed from more than one part, and which would otherwise result in particulate or adhesive contamination of the culture chamber, may desirably be formed as described herein. Examples of such vessels include T-flasks, HYPERFLASK cell culture vessels (Corning, Inc.), CELLSTACK culture chambers (Corning, Inc.), CELLCUBE modules (Corning, Inc.), CELL FACTORY culture apparatuses (Nunc, Intl.), and cell culture articles as described in WO 2007/015770, entitled "MULTI-LAYERED CELL CULTURE APPARTUS", and published Feb. 8, 2007, which publication is hereby incorporated by reference in its entirety to the extent that it does not conflict with the disclosure presented herein.

Figure 1B:
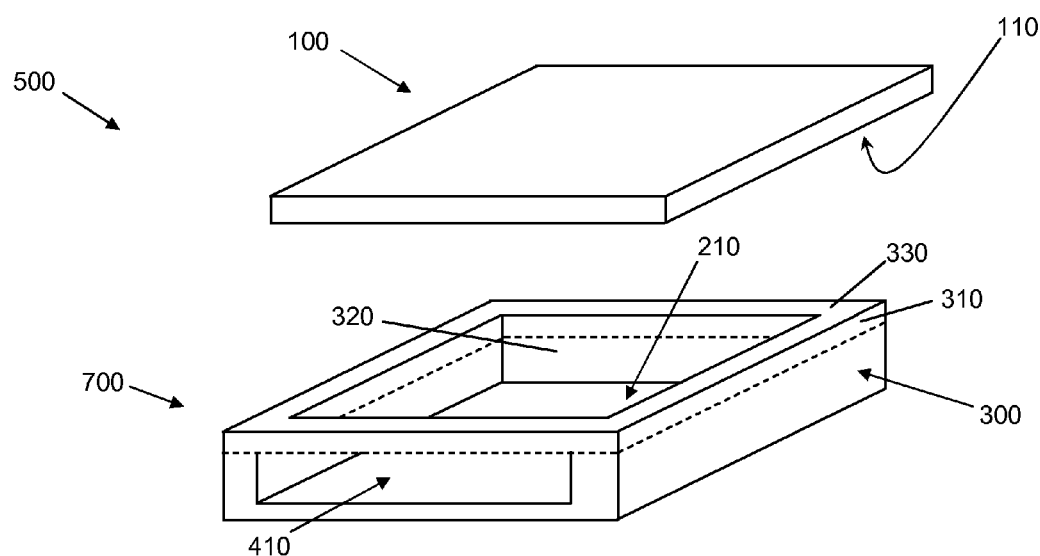
FIG. 1B is a schematic exploded perspective view of a representative cell culture assembly.
Figure 1C:
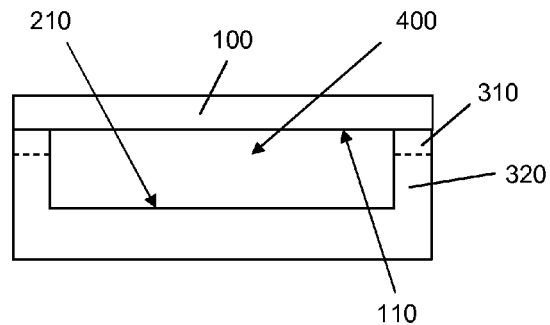
FIG. 1C is a schematic cross section of the cell culture assembly taken at line 1c-1c of FIG. 1A.

Referring to FIGS. 1A-C, a perspective view (1A), an exploded view (1B), and a cross section (1C) of a representative cell culture assembly 500 are shown. The assembly 500 includes a chamber 400 for culturing cells. The chamber 400 of the assembly 500 is formed by a first major surface 110, an opposing and spaced apart second major surface 210 and a sidewall 300 extending between the first major surface 110 and the second major surface 210. A portion 310 of the sidewall 300 proximate the first major surface 110 is formed from a material including an infrared absorbent material. A portion 320 of the sidewall 300 proximate the second major surface 210 is formed from a substantially non-infrared absorbing material. A dashed line is shown in FIGS. 1A-C to illustrate a distinction between the portion 310 of the sidewall 300 having substantially no infrared absorbing material and the portion 320 of the sidewall 310 having infrared absorbing material. Of course, such a sharp linear distinction may not exist, but rather an irregular distinction, gradual shift or gradient, or the like may exist.

A molded frame 700 may form the second major surface 210 and the sidewall 300 of the cell culture assembly 500. Of course, a multipart assembly may form the second major surface 210 and the sidewall 300. An opening 410 may be formed in the sidewall 300. The opening 410 may be formed during molding of the sidewall 300 or frame 700 including the sidewall 300, may be laser cut, punched out, or the like. The opening 410 is in fluid communication with the cell culture chamber 400 and provides access to the chamber 400 for introduction to or removal of cell culture fluid, cells or the like. The first major surface 110 may be formed of a polymeric film 100 that is permeable to gas and is impermeable to cell culture liquid.

An edge, ridge or rim 330 is formed by the infrared absorbing portion 310 of the sidewall that extends around the sidewall 300 and forms a seal with the polymeric film 100. The film 100 may fuse with the edge, ridge or rim 330 to form a hermetic seal and become integral with the sidewall 300 or frame 700. The infrared absorbing portion 310 of the sidewall 300 may be of any suitable thickness to sufficiently melt and form a bond with the polymeric film 100 when subjected to an IR welding process. When the sidewall 300 or frame 700 including the sidewall 300 is formed by a molding process as described below, the thickness of the infrared absorbing portion 310 extending around the edge of the sidewall 300 is typically about 0.5 millimeters or more; e.g., between about 0.5 and about 2 millimeters. If the infrared absorbing portion 310 of the sidewall 300 includes a material that can render the portion 310 optically non-transparent, such as carbon black, it may be desirable to limit the thickness of the infrared absorbing portion 310. Alternately, it may be desirable to select an infrared absorbing material or dye, such as IR-792 perchlorate available from ALDRICH CHEMICAL, which should not render an otherwise optically transparent side wall non-optically transparent.

Examples of infrared transparent materials that may be used to form the portion 320 of the sidewalls 300 proximate the second major surface 210, include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers. Such materials are also suitable for forming the frame 700 or other part defining the second major surface 210 or for forming the film. The portion 310 of the sidewall 300 proximate the film 100 may also be made of such materials with an infrared absorbing material being included. Examples of infrared absorbing materials that may be included in polymeric materials, e.g. by blending prior to polymerization or curing, include carbon black particle, laser dye molecules, or other IR absorbent materials commonly known to those of skill in the art. Carbon black particles may be advantageously included in a polymeric material for use in forming cell culture articles, as carbon black particles do not significantly migrate from most polymeric materials In various embodiments, substantially all of the components of an assembly are formed from the same or similar polymeric materials, such as polystyrene. In various embodiments, materials for forming cell culture articles as describe herein are optically transparent.

The frame 700 or sidewall 300 in various embodiments is rigid. Rigidity of the frame 300 or sidewall 300 is a factor of the polymeric material from which the frame 700 or sidewall 300 is formed and the thickness of the frame 700 or sidewall 300. In some embodiments, the frame 700 or sidewall 300 has a thickness of between about 1 mm and about 2.5 mm.

Any suitable polymeric film 100 may be employed according to the teachings presented herein. Preferably the polymeric film 100 is non-toxic to cells being cultured and compatible with cell culture media and components thereof. The polymer film 100, in many embodiments, is permeable to gas but impermeable to liquid cell culture media. Being permeable to gas, allows exchange of gasses across the film 100, which can allow oxygenation of cell culture medium within the chamber 400. Examples of suitable gas permeable polymeric materials useful for forming a film 100 include polystyrene polystyrene, polyethylene, polycarbonate, polyolefin, ethylene vinyl acetate, polypropylene, polysulfone, polytetrafluoroethylene (PTFE) or compatible fluoropolymer, a silicone rubber or copolymer, poly(styrene-butadiene-styrene) or combinations of these materials. As manufacturing and compatibility for the growth of cells permits, various polymeric materials may be utilized. Preferably the film 100 is of a thickness that allows for efficient transfer of gas across the film. For example, a polystyrene film 100 may be of a thickness of about 0.003 inches (about 75 micrometers) in thickness, though various thicknesses are also permissive of cell growth. As such, the membrane may be of any thickness, preferably between about 25 and 250 micrometers, or between approximately 25 and 125 micrometers. The membrane 100 allows for the free exchange of gases between the chamber 400 of the assembly 500 and the external environment and may take any size or shape. Preferably, the membrane 100 is durable for manufacture, handling, and manipulation of the apparatus.

A cell culture assembly 500, as described herein, may have any suitable overall dimensions. Preferably, the dimensions of the assembly 500 are sufficient to culture cells for their intended purpose. For example, in various embodiments, the volume of the cell culture chamber 400 is between about 0.1 ml cm$^2$ and about 0.5 ml/cm$^2$.

The first major surface 110 formed by the film 100 or the second major surface 210 formed by the frame 700 is supportive of cell growth, attachment, differentiation, or the like. If cells are cultured on the first major surface 110 formed by the film 100, exchange of gasses across the film 100 to support cell culture may be maximized. When cells are cultured on the second major surface 210, it may be desirable to fully fill the chamber 400 to maximize exchange of gasses between the culture media and the external environment across the membrane 100.

Prior to, or after, sealing the film 100 to the sidewall 300 via infrared radiation, the major surface 110 of the film 100, the interior surface of the sidewall 300 or the second major surface 210 may be treated or coated to facilitate cell culture. Treatment may be accomplished by any number of methods known in the art which include plasma discharge, corona discharge, gas plasma discharge, ion bombardment, ionizing radiation, and high intensity UV light. Coatings can be introduced by any suitable method known in the art including printing, spraying, condensation, radiant energy, ionization techniques or dipping. The coatings may then provide either covalent or non-covalent attachment sites. Such sites can be used to attach moities, such as cell culture components (e.g., proteins that facilitate growth or adhesion). Further, the coatings may also be used to enhance the attachment of cells (e.g., polylysine).

Figure 1D:
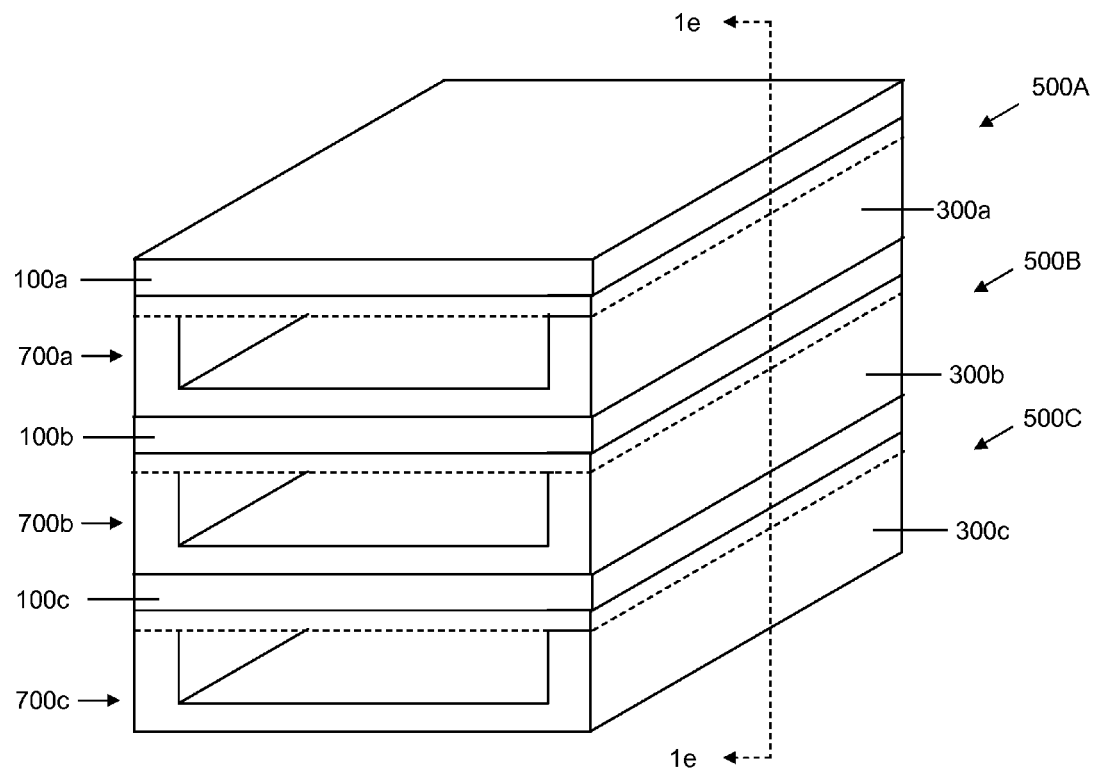
FIG. 1D is a schematic perspective view of representative stacked cell culture assemblies.
Figure 1E:
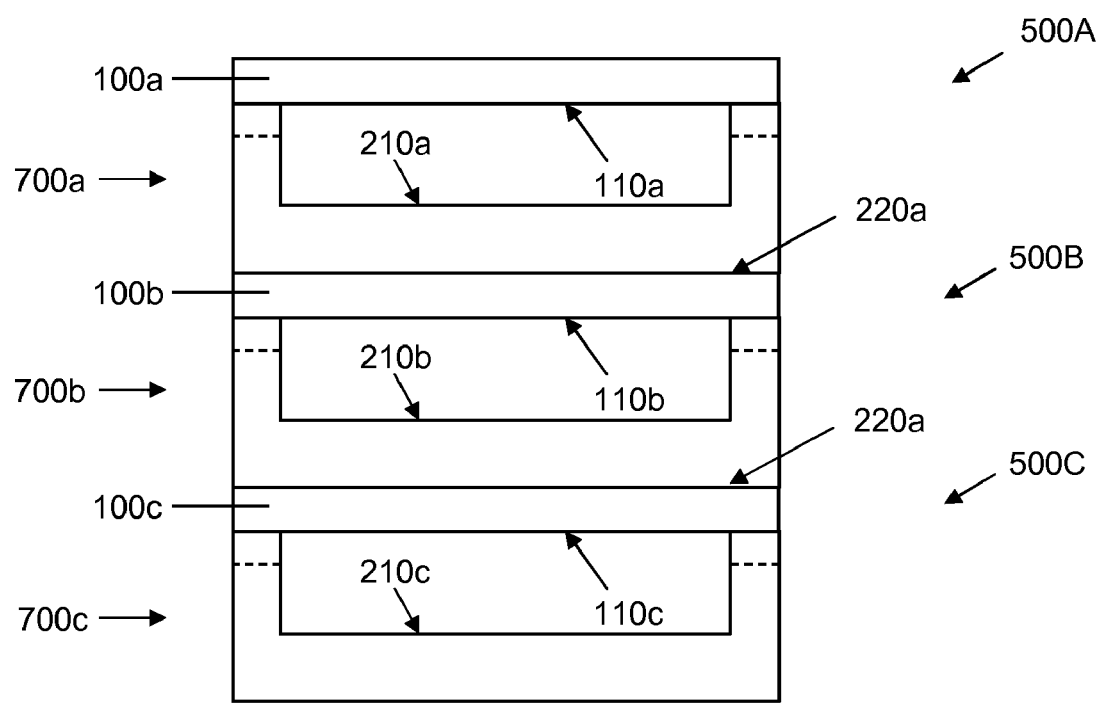
FIG. 1E is a schematic cross section of the stacked cell culture assemblies taken at line 1e-1e of FIG. 1D.

Referring now to FIGS. 1D-E, a plurality of the cell culture assemblies 500A, 500B, 500C may be disposed in a stacked arrangement. In the depicted embodiments, the sidewalls 300a, 300b, 300c of the stacked assemblies 500A, 500B, 500C are substantially aligned. The polymer film 100b of the second assembly 500B is disposed in proximity to the bottom 220a of the frame 700a of the first assembly 500A. Accordingly, the second major surface 210a of the first assembly 500A is proximate the first major surface 110b of the second assembly 500B. Additional assemblies may be stacked in a similar manner. For example, the stack may include a third assembly 500C where the polymer film 110c of the third assembly 500C is disposed in proximity to the bottom of the frame 700b of the second assembly 500B. While three assemblies are shown in FIGS. 1D-E, it will be understood that any number of assemblies may be stacked.

Figure 2A:
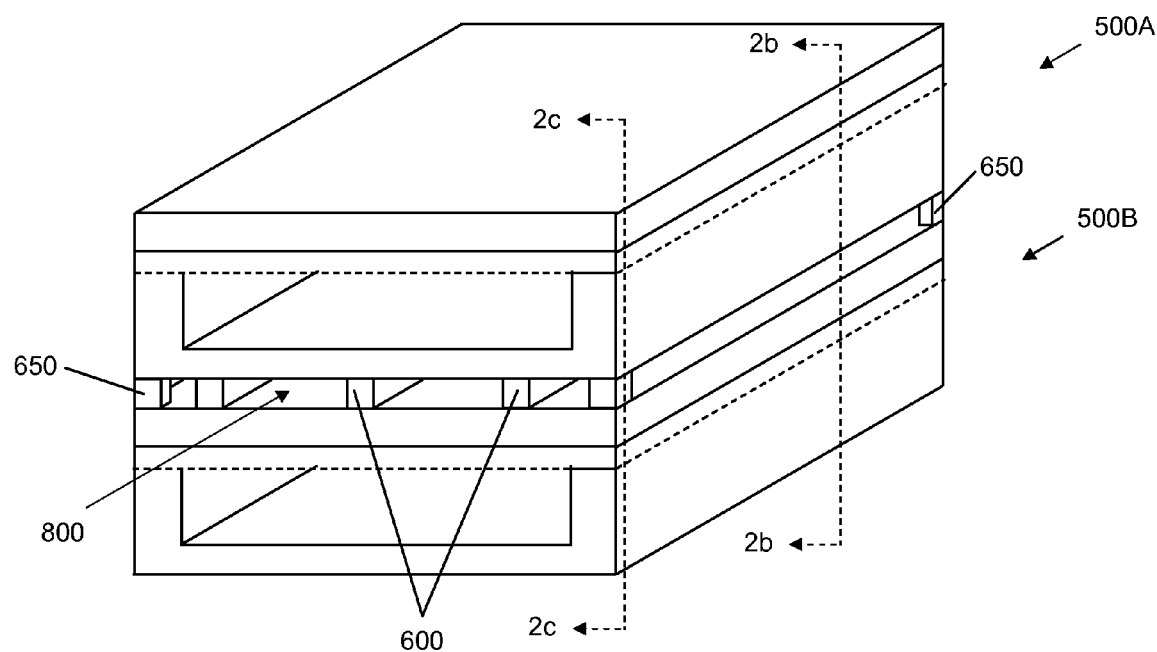
FIG. 2A is a schematic perspective view of representative stacked cell culture assemblies.
Figure 2B:
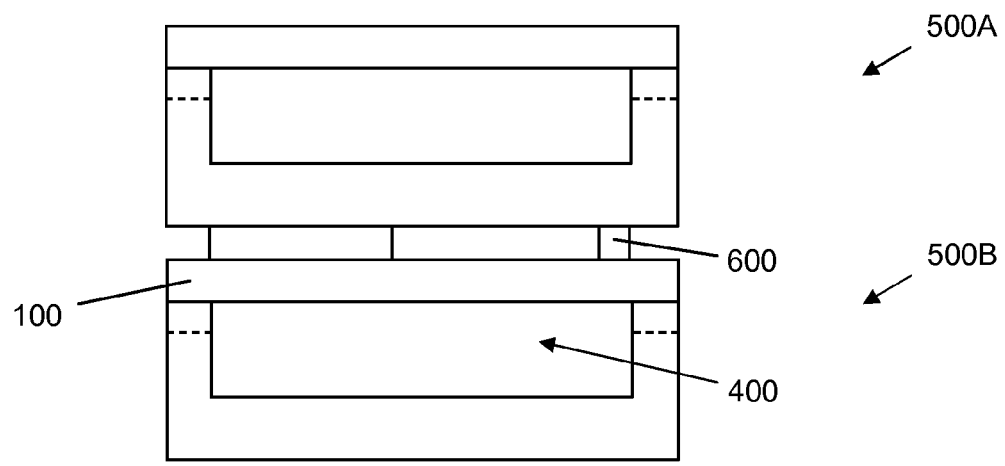
FIG. 2B is a schematic cross section of the stacked cell culture assemblies taken at line 2b-2b of FIG. 2A.
Figure 2C:
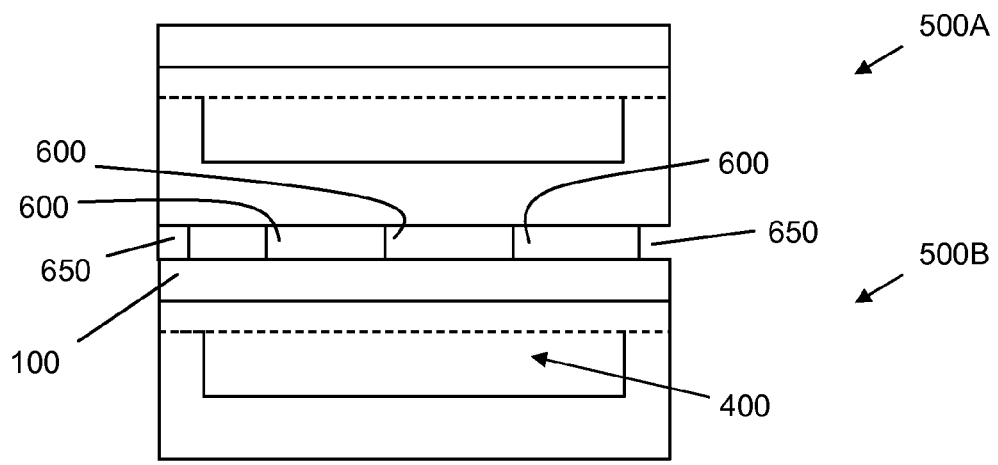
FIG. 2C is a schematic cross section of the stacked cell culture assemblies taken at line 2c-2c of FIG. 2A.

In many embodiments, a spacer layer or spacers are provided between stacked cell culture assemblies to provide a passageway for flow of air along the polymeric film of the assembly. Referring now to FIGS. 2A-C, a perspective view (2A) and cross sections (2B-C) of stacked cell culture assemblies 500A, 500B are shown. A spacer layer or spacers 600 are disposed between the stacked assemblies 500A, 500B, forming a passageway 800 for air to flow. Such flow of air allows exchange of gases between chamber 400b and passageway 800 across the gas permeable film 100b. The spacer layer or spacers 600 may take any shape and may be formed of any suitable material. For example, the spacer layer or spacers 600 may be in the form of a corrugated sheet; blocks or strips that extend the length or width of cell culture assembly 500, frame or film; a plurality of discrete bumps; or the like. In some embodiments, a spacer layer or spacer 600 be formed from polymeric material. The spacer 600 or spacer layer may a separate part that may be inserted between cell culture assemblies 500A, 500B or may be attached to the bottom of a frame of a cell culture assembly 500A or to the top of a cell culture assembly 500B.

A spacer may be or include one or more standoffs 650 disposed between the assemblies 500A, 500B. The standoffs 650 are preferably configured and positioned to be aligned with the rim (see, e.g., element 330 in FIG. 1B) of the sidewall of the underlying assembly 500B to avoid damage to the underlying film 100. Any suitable standoff 650, such as a raised corner, a post, a ledge, or any other feature that will allow spacing between successively stacked assemblies, may be employed.

Figure 3A:
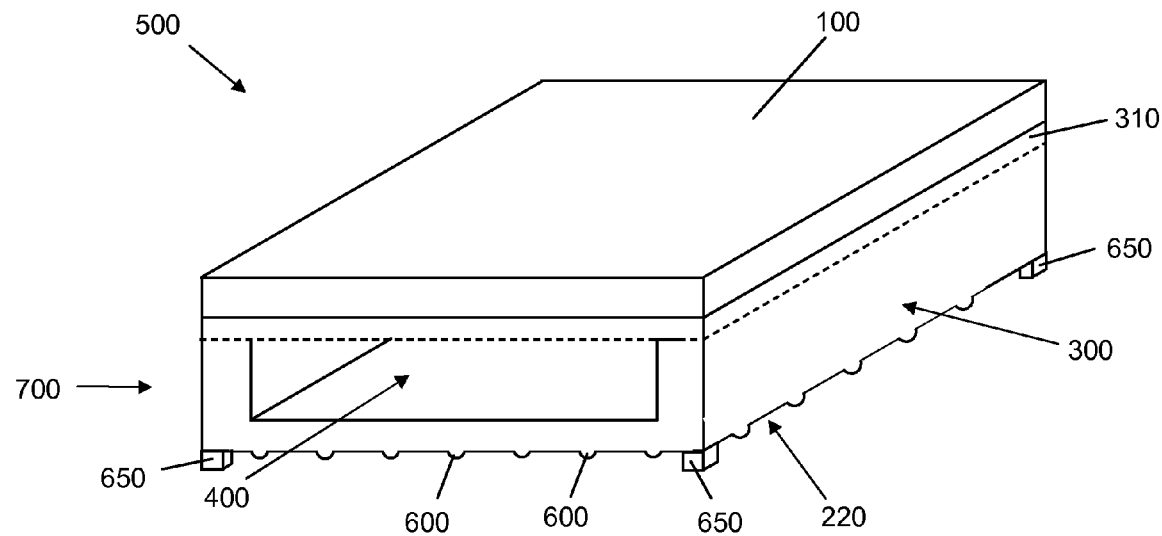
FIG. 3A is a schematic perspective view of a representative cell culture assembly.
Figure 3B:
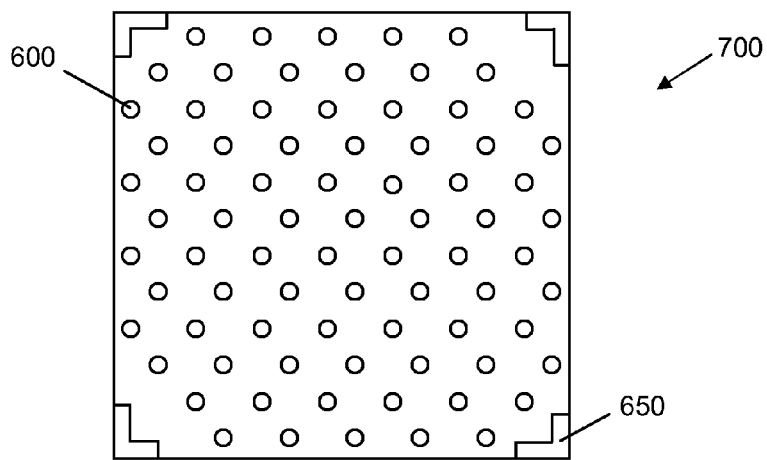
FIG. 3B is a bottom-up view of the cell culture assembly depicted in FIG. 3A.
Figure 3C:
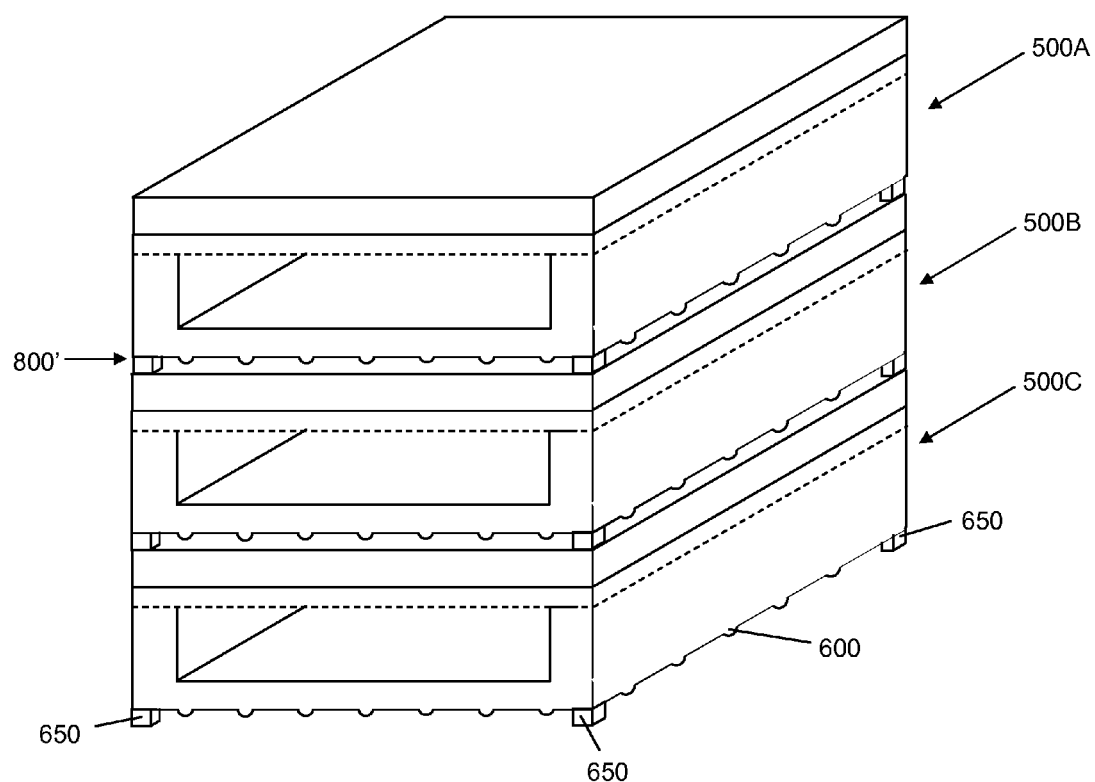
FIG. 3C is a schematic perspective view of representative stacked cell culture assemblies.

In various embodiments, the spacer layer or spacers 600 or the standoffs 650 are molded with and form part of the frame 700 of a cell culture assembly. For example, and referring to FIGS. 3A-C, a spacer layer or spacers 600 are integrated with a molded frame 700 of a cell culture assembly 500. In FIG. 3B, a bottom-up view of the cell culture assembly 500 of FIG. 3A is shown. The bottom of the molded frame 700 includes a plurality of spaced apart bumps serving as spacers 600. In the depicted embodiment, the spacers 600 are spaced apart to allow air to flow along the polymeric film 100 when assemblies 500A, 500B, 500C are stacked as shown, e.g., in FIG. 3C.

Figure 4A:
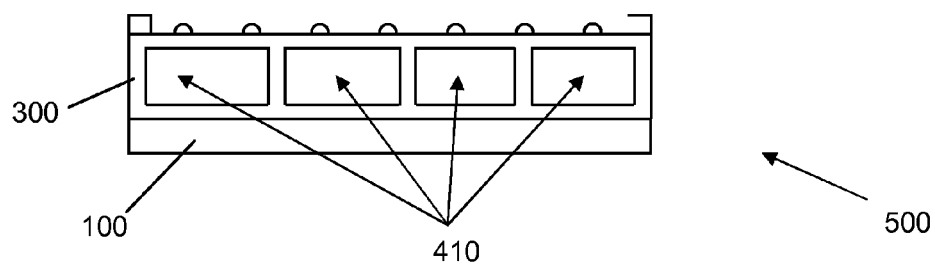
FIG. 4A is a schematic front view of a representative cell culture assembly.
Figure 4B:
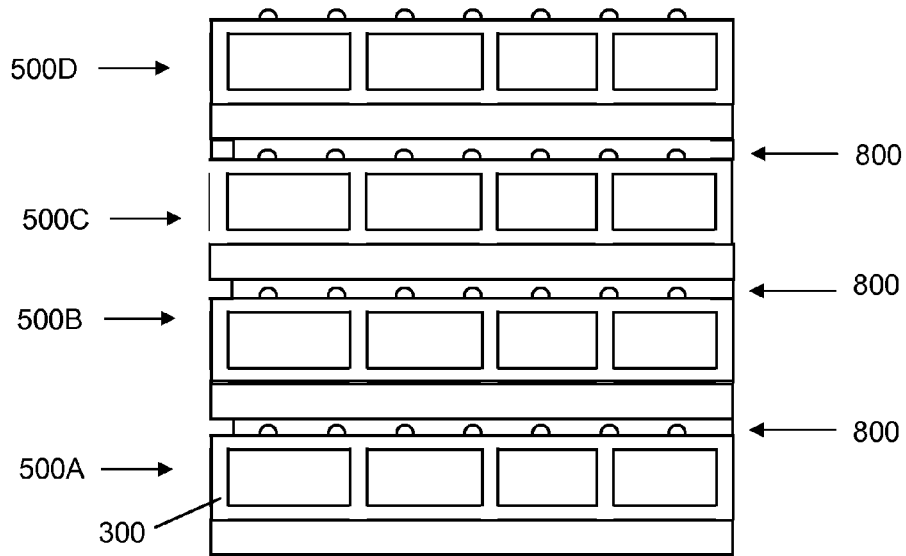
FIG. 4B is a schematic front view of representative stacked cell culture assemblies.

Referring now to FIGS. 4A-B, in which front views of a cell culture assembly 500 and stacked assemblies 500A, 500B, 500C, 500D are shown, more than one opening 410 may be formed by side wall 300 to provide access the cell culture chamber. By having multiple openings 410, as opposed to one large opening, the front surface area of the sidewall 300 around the opening increases. The increased surface area can allow for improved bond strength or generally connectability with a port or adaptor that may be used to connect multiple cell culture assemblies.

Figure 5A:
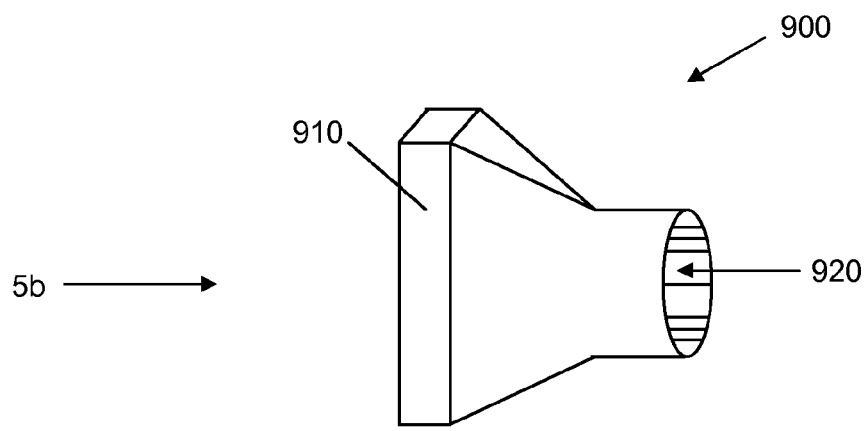
FIG. 5A is a schematic perspective view of a representative adaptor for a cell culture article.
Figure 5B:
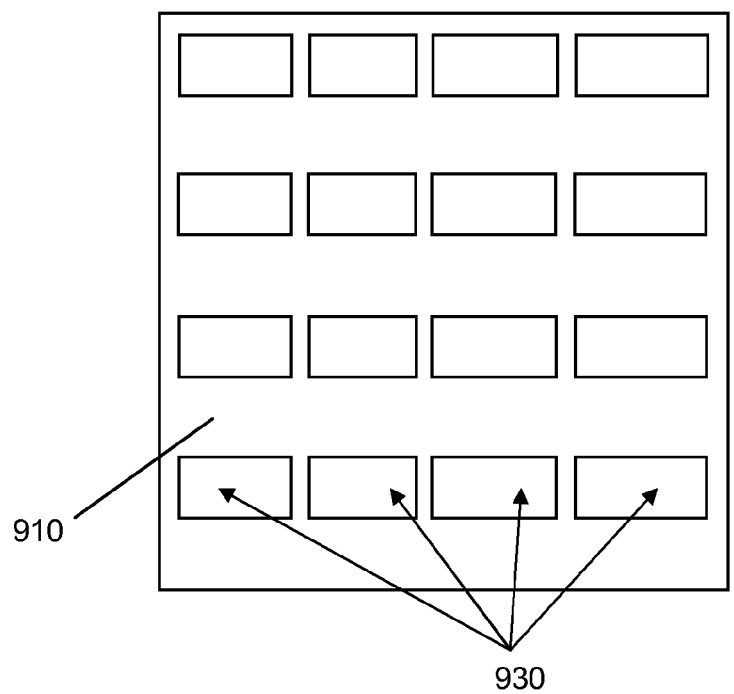
FIG. 5B is a schematic front view of the adaptor viewed along line 5b of FIG. 5A.

For example, and referring to FIGS. 5A-B and adaptor 900 for connecting to a cell culture assembly or stacked cell culture assemblies is shown. The adaptor 900 depicted in FIG. 5A is in the general shape of a neck of a culture flask. The adaptor 900 includes a housing 910 that forms a port 920 that can serve as an inlet or outlet for a cell culture article. As shown in the embodiment depicted in FIG. 5B, which is a view along line 5b of an embodiment of the adaptor 900 of FIG. 5A. The depicted face of the adaptor 900 includes a plurality of openings 930 formed in the adaptor housing 910. The openings 930 are in fluid communication with the port 920. The openings 930 are configured to align with openings formed in the sidewalls of cell culture assemblies. In the embodiment depicted in FIG. 5B, the openings 930 in the adaptor housing 910 are configured and positioned to align with corresponding openings in the sidewalls 300 of the stacked cell culture assemblies 500A, 500B, 500C, 500D depicted in FIG. 4B. When the openings 930 of the adaptor 900 are fluidly coupled with the openings 600 in the sidewalls 300 of the culture assembly, 500A, 500B, 500C, 500D, the port 920 of the adaptor 900 is in fluid communication with the chambers of the cell culture assemblies 500A, 500B, 500C, 500D. A cap (not shown) or septum (not shown) may used to seal port 920.

Figure 6A:
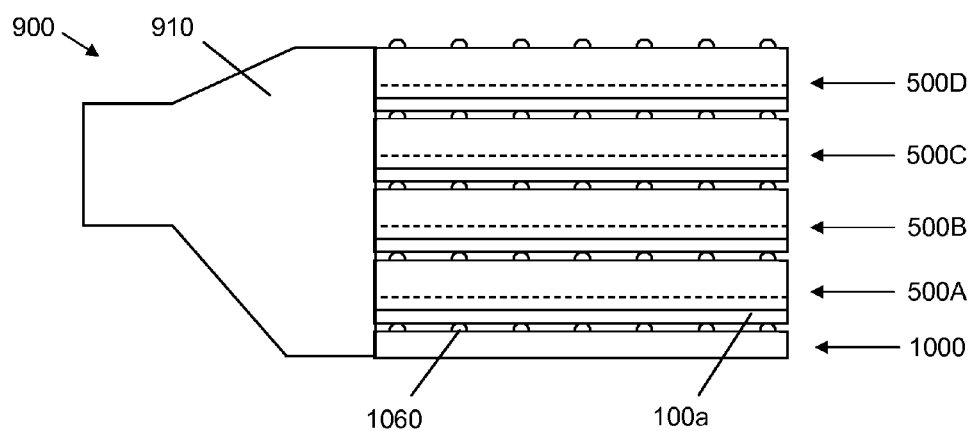
FIGS. 6A-C are schematic side views of representative cell culture articles containing multiple cell culture assemblies.
Figure 6B:
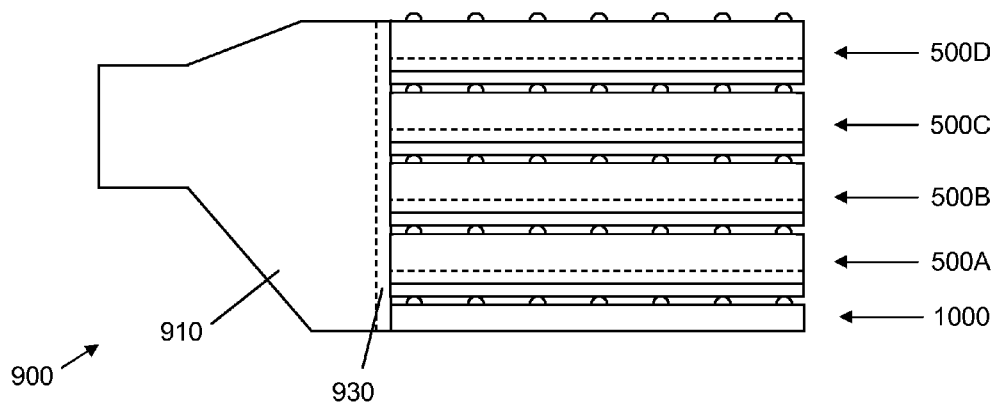
Figure 6C:
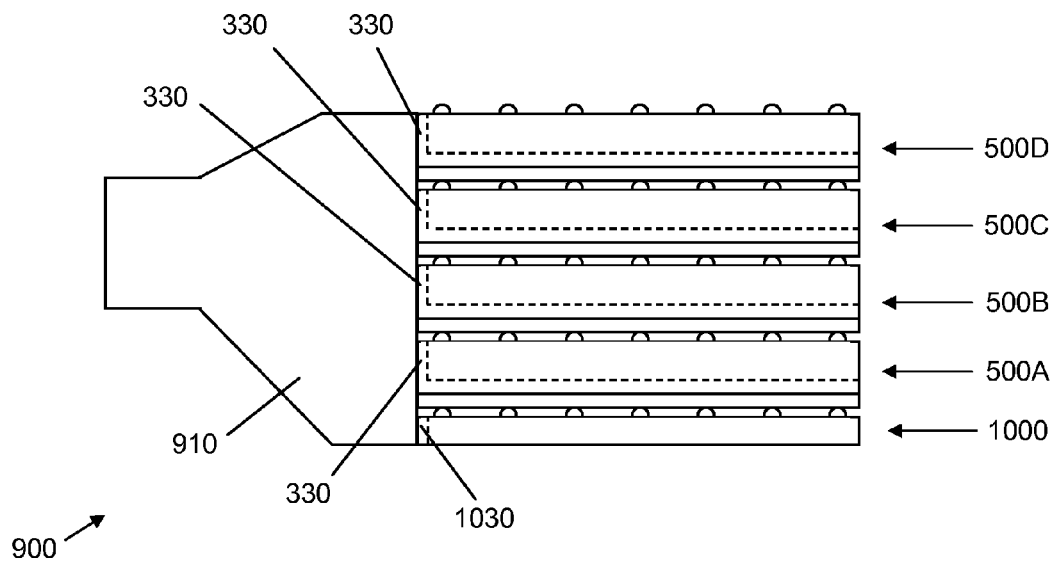

Referring now to FIGS. 6A-C, side views of cell culture articles in which stacked cell culture assemblies 500A, 500B, 500C, 500D are coupled with an adaptor 900 are shown. As depicted, a plate 1000 may be positioned to protect, e.g. may be disposed on top of, the polymeric film 110a of the cell culture assembly 500A that would otherwise be exposed by stacking of the assemblies 500A, 500B, 500C, 500D. Spacers 1060 to allow air flow along the film 110a may be disposed between the plate 1000 and the membrane 100a. The spacers 1060 may be a separate part or may be molded as part of the plate 1000.

Still with reference to FIGS. 6A-C, an adaptor 900 may be coupled or connected to one or more of the assemblies 500A, 500B, 500C, 500D or plate 1000 in any suitable manner. With reference to FIG. 6B, the front face of the adaptor housing 910, i.e. the face of the adaptor 900 in which openings are formed (see e.g. FIG. 5B), may include a infrared absorbent material for facilitating IR welding to the assemblies 500A, 500B, 500C, 500D or plate 1000. In many embodiments, and with reference to FIG. 6C, the front face of the assemblies 500A, 500B, 500C, 500D or plate 1000 may include a infrared absorbent material for facilitating IR welding to the adaptor 900. The adaptor 900 and plate 1000 may be formed from any suitable material, such as polymeric material, which may be similar to, or the same as those, that are suitable for forming the assemblies 500A, 500B, 500C, 500D.

The various assemblies 500A, 500B, 500C, 500D and plate 1000 may be held together at one or more locations away from the adaptor 910. For example, adhesives, or spot welds, e.g. at standoffs (not shown in FIG. 6A-C), may be used to secure the positional relationship of the assemblies relative to each other.

Figure 7A:
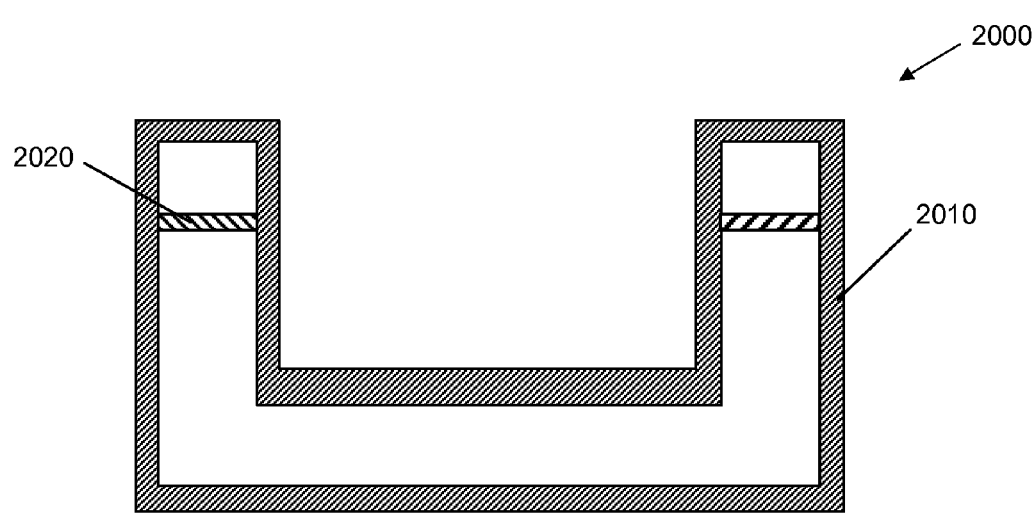
FIGS. 7A-D are schematic cross sections of a representative mold and show sequential forming of a representative cell culture assembly frame within the mold.

Referring now to FIG. 7A, a cross section of a mold 2000 that may be used to form a frame of a cell culture assembly having a portion with substantially non-infrared absorbent material and a portion with infrared absorbing material is shown. The mold 2000 includes a housing 2010 and a separating member 2020 disposed within and moveable within or removable from the housing 2010. The mold 2000 and separating member 2020 may be formed of any suitable material, such as, for example, hardened tool steel.

Figure 7B:
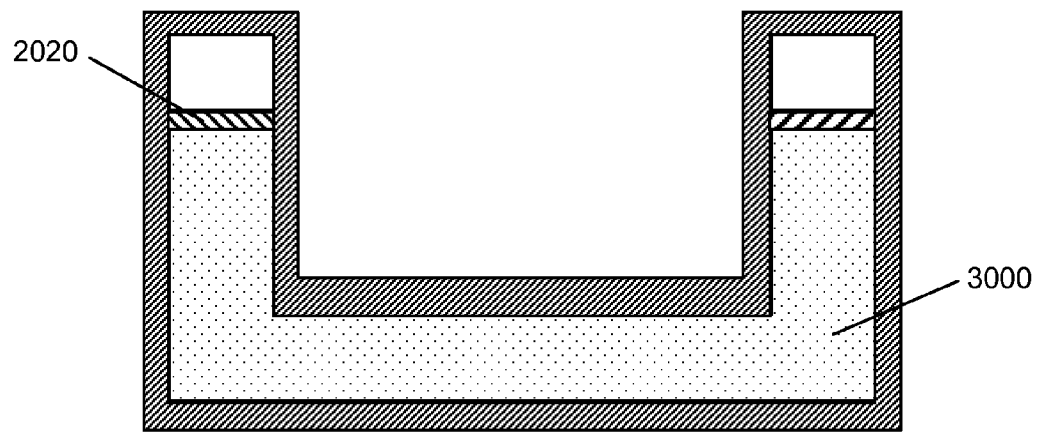
Figure 7C:
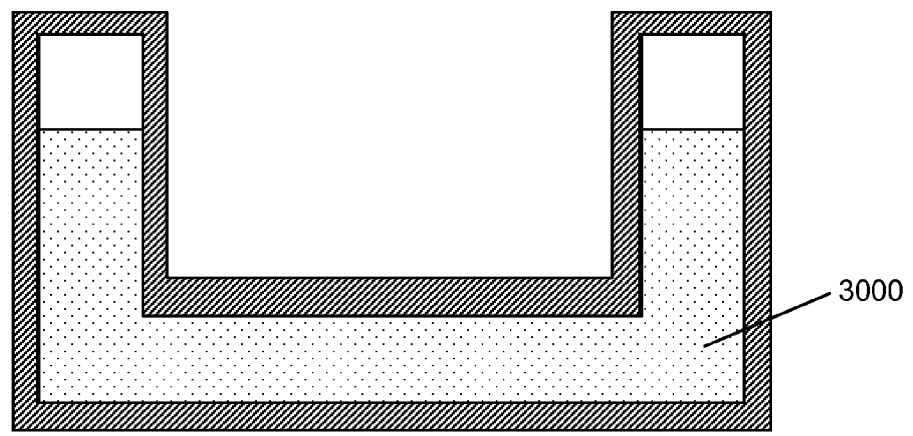
Figure 7D:
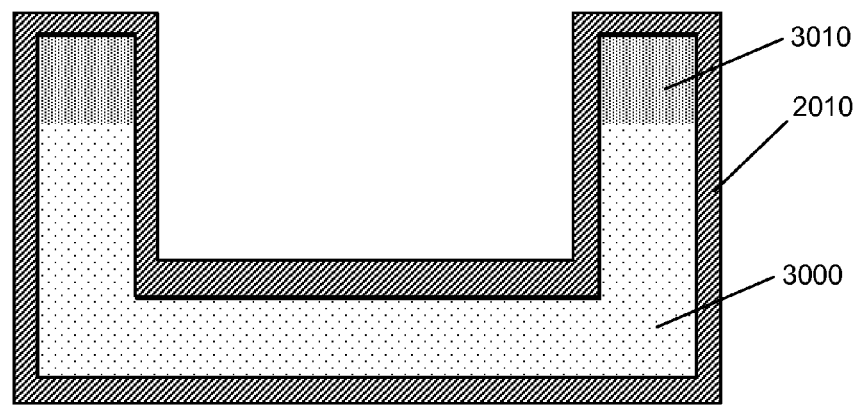
Figure 7E:
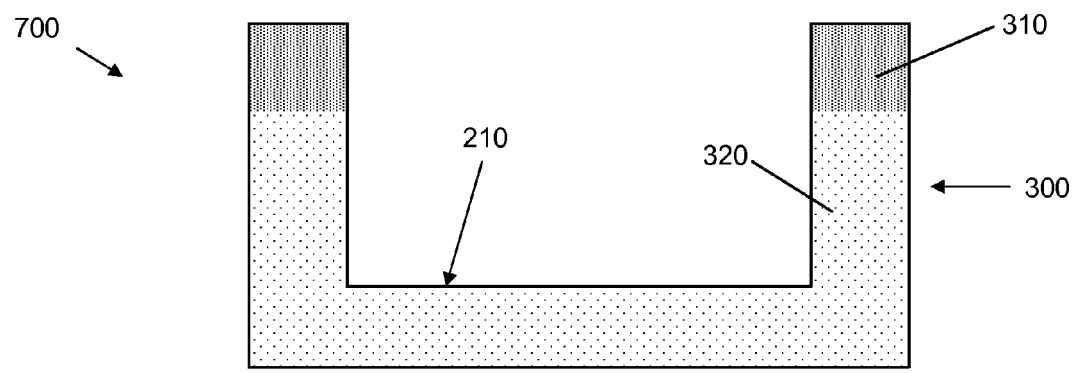
FIG. 7E is a schematic cross section of the cell culture assembly frame formed within the mold of FIGS. 9A-D.

A process for forming a frame of a cell culture assembly as described herein is shown in FIGS. 7B-E. As shown in FIG. 7B, a first material 3000 that is substantially non-infrared absorbent is introduced, e.g. by injection, into the mold 700. The separating member 2020 is then moved or removed (compare FIG. 7B to FIG. 7C) and a material 3010 including an infrared absorbent agent is introduced, e.g. by injection, into the mold 2000 (FIG. 7D). The frame 700 is removed from the mold, resulting in a frame 700 having a surface 210 and sidewalls 300 for forming a chamber in which cells may be cultured. The portion 320 of the sidewall 300 proximate the surface 210 is substantially non-infrared absorbing, and the portion 310 of the sidewall 300 distal the surface 210 includes infrared absorbing material. It will be understood that a similar two shot injection molding process may be used to make a frame with a front face having an infrared absorbing material (see, e.g., FIG. 6C) or an adaptor having a face with an infrared absorbing material (see, e.g., FIG. 6B).

While not shown, the mold 2000 may be shaped and configured to form any frame suitable for culturing cells. For example, the mold may be shaped and configured to form a frame of a cell culture assemble as depicted in any of FIGS. 1-4 and 6. For example, the mold may be shaped to form a frame having one or more openings. Of course and opening may be formed in the sidewall after being molded, e.g. by laser cutting, punching out, or the like.

Figure 7F:
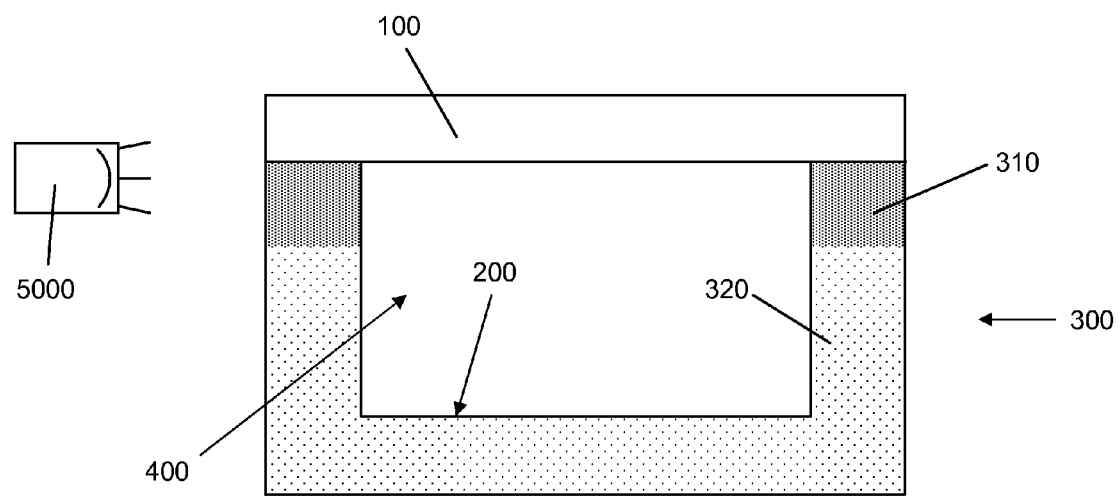
FIG. 7F is a schematic cross section of the frame of FIG. 9E and a representative film and a block drawing of an infra-red emitting source directed at the frame and film.

Referring now to FIG. 7F, a polymeric film 100 may be contacted with the portion 320 of the sidewall 300 having the IR absorbent material to form an interface between the sidewall 300 and the film 100. Infrared radiation from an infrared source 5000 may be directed at the interface to sufficiently melt the infrared absorbent portion 310 to sufficiently melt the portion 310 of the sidewall 300 to bond the sidewall 300 of the frame to the film to form a sealed chamber 400 formed by the film 100, the surface 200 of the frame, and the sidewall 300 of the frame. In various embodiments, the IR welding process is performed substantially as described in US 2005/0047971, entitled "MULTI-WELL PLATE AND METHOD OF MANUFACTURE", published Mar. 3, 2005, which publication is hereby incorporated herein in its entirety to the extent that it does not conflict with the disclosure presented herein. If an infrared absorbing transparent pigment, such as IR-792 perchlorate, is used, concentrations are preferably greater than $5 \times 10^{-6}$ g/cm$^2$ at the interfacial region between the film 100 and the sidewall 300. Carbon black particles may be used at any suitable concentration. For example, the concentration of carbon black particles maybe between about 0.01% and about 5% by weight, or between about 0.1% and about 1% by weight.

The film 100 is firmly held against the sidewall 300, e.g. with an infrared assembly machine such as those manufactured by Branson Ultrasonics (Danbury, Conn.). During the infrared welding process, clamps or bladders are use to retain firm pressure (e.g. between about 4 and 25 psig) between film 100 and sidewall 300. The infrared welding process may take place under an appropriate gas, such as nitrogen. IR energy may then be supplied by an array of infra red laser diodes transmitting at approximately 820 nm and directed to the interface between the film and the sidewall. The infrared absorbing molecules forming part of the matrix polymer of the IR absorbing portion 310 of the sidewall 300, absorb this energy, transfer it to the polymer and thereby melt the portion of the sidewall 300 that interfaces the film 100. Assembly preferably takes place under clean room conditions. In fact, a carbon filter within the unit will effectively remove smoke and residual organics created from the welding process, as well as protect the lasers from out-gassing, and add clean air to the system. Further, it is helpful to sparge the unit with helium while the welding process is initiated and carried out. This helps achieve a clean part and limits any unwanted surface oxidation or other reactions on the exposed surfaces.

The array of infrared diodes may be focused to give a uniform line of energy about 2 mm wide. The line of energy may be scanned over the entire surface to be bonded. The scan speed is variable, but preferably in the range of 0.1-1.0 inches/second. Operation power on the instrument is typically in the range between 45 and 75%.

Thus, embodiments of ASSEMBLY OF CELL CULTURE VESSELS are disclosed. One skilled in the art will appreciate that the cell culture assemblies, vessels, and methods described herein can be practiced with embodiments other than those disclosed. The disclosed embodiments are presented for purposes of illustration and not limitation.

What is claimed is:

1. A cell culture apparatus comprising:
   At least a first cell culture chamber and at least a second cell culture chamber, each cell culture chamber comprising:
   top surface formed by a gas permeable polymeric film that is impermeable to cell culture liquid
   an opposing bottom surface spaced apart from the top surface, and
   a side-wall extending between the top surface and the bottom surface,
   wherein the bottom surface and the sidewall are formed together as a molded frame, and
   wherein a portion of the sidewall proximate to the top surface comprises an infrared absorbent material and a portion of the first sidewall proximate to the bottom surface comprises non-infrared absorbent material;
   wherein the first cell culture chamber and the second cell culture chamber are disposed in a stacked arrangement such that the sidewalls of the first cell culture chamber are substantially aligned with the sidewalls of the second cell culture chamber; and
   wherein the bottom surface of the first cell culture chamber is spaced apart from the top surface of the second cell culture chamber.

2. The cell culture apparatus of claim 1, wherein an opening in fluid communication with a cell culture chamber is formed within the sidewall.

3. The cell culture apparatus of claim 1, wherein the molded frame and the polymeric film comprise polystyrene.

4. The cell culture apparatus of claim 3, wherein the infrared absorbent material comprises carbon black particles.

5. The cell culture apparatus of claim 1, wherein a first opening in fluid communication with the first cell culture chamber is formed in the sidewall of the first frame and a second opening in fluid communication with the second cell culture chamber is formed in the sidewall of the frame of the second chamber.

6. The cell culture apparatus of claim 5, further comprising an access port in fluid communication with the first and second openings.

7. The cell culture apparatus according to claim 1, further comprising spacers between stacked cell culture chambers to provide the space between the bottom surface of the first cell culture chamber and the top surface of the second cell culture chamber.

8. A method for forming a cell culture apparatus according to claim 1, the method comprising:
   molding a first frame, the first frame comprising an optically transparent bottom surface and a sidewall extending from the bottom surface, sidewall having an optically transparent portion proximate to the bottom surface and an infrared absorbent portion distal to the bottom surface,
   wherein the molding comprises:
      introducing a first polymeric composition into a mold for forming the transparent bottom surface and the transparent portion of the sidewall and
      introducing into the mold a second polymeric composition including an infrared absorbent material for forming the infrared absorbent portion of the sidewall distal to the bottom surface;
   contacting the infrared absorbent portion of the sidewall to a gas permeable polymeric film at an interface between the sidewall and the gas permeable polymeric film;
   directing infrared radiation to the interface to sufficiently melt the infrared absorbent portion of the first sidewall to sealingly bond the frame to the gas permeable polymeric film such that a first chamber for culturing cells is formed by the first film, the sidewall and the bottom surface.

9. The method of claim 8, further comprising:
   molding a second frame having a structure substantially the same as the first frame, the second frame comprising an optically transparent bottom surface and a sidewall extending from the bottom surface, the sidewall having an optically transparent portion proximate to the bottom surface and an infrared absorbent portion distal to the bottom surface,
   wherein the molding comprises:
   introducing a first polymeric composition into a mold for forming the transparent bottom surface and the transparent portion of the sidewall of the second chamber and,
   introducing into the mold a second polymeric composition including an infrared absorbent material for forming the infrared absorbent material for forming the infrared absorbent portion of the sidewall distal to the bottom surface; and
   contacting the infrared absorbent portion of the sidewall to a gas permeable polymeric film at an interface between the sidewall and gas permeable polymeric film;
   directing infrared radiation to the interface to sufficiently melt the infrared absorbent portion of the sidewall to sealingly bond the frame to the gas permeable polymeric film such that a second chamber for culturing cells is formed by the gas permeable polymeric film, the sidewall and the bottom surface.

10. The method of claim 8, wherein the first frame and the first film comprise polystyrene.

11. The method of claim 10, wherein the infrared absorbent portion of the sidewall comprises carbon black particles.

12. The method of claim 8, further comprising forming a first opening in the sidewall of the first chamber.

13. The method of claim 12, wherein the opening is formed in the first sidewall during the molding of the first frame.

14. The method of claim 9, wherein the infrared absorbent material comprises carbon black particles.

15. The method of claim 9, further comprising
forming a second opening in the sidewall of the second frame.

16. The method of claim 15, further comprising:
stacking the first and second chambers such that the first and second sidewalls are substantially aligned, the bottom surface of the first frame is spaced apart from the gas permeable film of the second chamber, and a tracheal chamber is formed between the bottom surface of the first frame and the gas permeable film of the second chamber.

17. The method of claim 16, further comprising:
aligning first and second openings of an adaptor with the first opening of the first sidewall and the second opening of the second sidewall;

contacting the adaptor with first and second sidewalls to form first and second interfaces between the first sidewall and the adaptor and the second sidewall and the adaptor; and directing infrared radiation at the first and second interfaces between the first sidewall and the adaptor and the second sidewall and the adaptor to sufficiently melt the infrared absorbent portion of the first and second sidewalls to bond the first and second frames to the adaptor.

18. The method of claim 17, wherein the adaptor comprises an access port forming fluid communication pathways between the adapter and the first cell culture chamber through the first openings of the adaptor, through the first opening of the first sidewall into the first cell culture chamber; and between the adapter and the second cell culture chamber through the second opening of the adaptor, through the second opening of the second sidewall into the second cell culture chamber.

19. The method of claim 18, wherein the adapter comprises a neck piece defining an access port to the adaptor such that the access port is in fluid communication with the first and second openings of the adaptor.

\* \* \* \* \*